United States Patent [19]

Royster, Jr. et al.

[11] Patent Number: 5,856,080
[45] Date of Patent: Jan. 5, 1999

[54] PREPARATION AND USE OF A DIMETHYLAMINE SILVER CHLORIDE COMPLEX AS A SINGLE SOURCE PRECURSOR FOR NUCLEATION OF SILVER CHLORIDE CRYSTALS

[75] Inventors: Tommie L. Royster, Jr.; Seshadri Jagannathan, both of Rochester; David G. Juhas, Webster; Heinz E. Stapelfeldt, Pittsford, all of N.Y.

[73] Assignee: Eastman Kodak Company, Rochester, N.Y.

[21] Appl. No.: 866,785

[22] Filed: May 30, 1997

[51] Int. Cl.$^6$ .......................... G03C 1/005; C01G 5/00; C01G 5/02; C07F 1/10
[52] U.S. Cl. .......................... 430/569; 423/23; 423/42; 117/938; 205/507; 556/110
[58] Field of Search .......................... 430/569; 423/23, 423/42; 117/938; 205/507; 556/110

[56] References Cited

U.S. PATENT DOCUMENTS

| | | | |
|---|---|---|---|
| 3,883,355 | 5/1975 | Walworth | 430/569 |
| 3,941,600 | 3/1976 | Walworth | 430/569 |
| 4,153,462 | 5/1979 | Gerber et al. | 430/569 |
| 4,340,666 | 7/1982 | Walworth | 430/569 |
| 5,478,718 | 12/1995 | Verbeeck et al. | 430/569 |
| 5,541,051 | 7/1996 | Verbeeck et al. | 430/569 |
| 5,604,087 | 2/1997 | Lapp et al. | 430/569 |
| 5,759,762 | 6/1998 | Budz et al. | 430/611 |

OTHER PUBLICATIONS

Aldrich Catalog, p. 566, No. 12,636–5, Aldrich Chemical Company, Milwaukee, WI, 1996.

*Primary Examiner*—Mark F. Huff
*Attorney, Agent, or Firm*—Arthur H. Rosenstein

[57] ABSTRACT

A dimethylamine silver chloride complex is used as a single source precursor for nucleation of silver chloride crystals.

5 Claims, No Drawings

PREPARATION AND USE OF A DIMETHYLAMINE SILVER CHLORIDE COMPLEX AS A SINGLE SOURCE PRECURSOR FOR NUCLEATION OF SILVER CHLORIDE CRYSTALS

FIELD OF THE INVENTION

This invention relates to the nucleation process of silver chloride crystals. In particular, it relates to the use of a unique silver halide complex contained in a dimethylamine solution that can be used as single source material for nucleation of silver chloride crystals.

BACKGROUND OF THE INVENTION

Silver halide emulsions are generally prepared using a reactive precipitation process; aqueous solutions of silver nitrate and alkali halides are reacted in the presence of gelatin. The composition of resultant product (silver halide emulsions) is tuned by varying the constituents of the alkali halide solution. For example, the precipitation of silver bromide emulsions is carried out using sodium bromide as the alkali halide, while silver chloride emulsions are precipitated using sodium chloride. Appropriate addenda/dopants are generally introduced as aqueous solutions during the precipitation process, to generate silver halide emulsions of desired composition.

The important feature of all these processes is the bimolecular chemical reaction between (Ag+) ions and the appropriate anion(s) to generate the precipitating species. It is possible to vary the chemical and the structural composition of the product emulsion by varying the constituents of the reagent solutions, but the chemical reaction responsible for the generation of the desired silver halide emulsion is always the reaction between (Ag+) ions that are present in a solution or on the surface of the silver halide emulsion, and the appropriate anion(s).

From an operational point of view, generation of silver halide emulsions by this reactive precipitation process involves the addition of concentrated reagent solutions into a reactor under vigorous mixing conditions. The goal of the mixing process is to minimize the volume of the reactor that is exposed to the unreacted reagent solutions. However, even under ideal mixing conditions, the volume of the reactor that is exposed to the unreacted reagents is finite and relatively large.

In order to understand the reasons for the exposure of the reactor contents to unreacted reagents it is necessary to examine the mechanism of the mixing process. Mixing in emulsion precipitation processes is achieved by means of a rapidly spinning rotary agitator. The momentum generated by the rotary agitator results in the circulation of the fluid in the reactor. Appropriate baffling devices are used to randomize the fluid motion in the reactor, to achieve efficient mixing. It is important to recognize that efficient mixing requires rapid circulation of the fluid in the reactor. In a typical emulsion generation process, the reagent solutions are introduced into a region of the reactor that experiences good mixing. Consequently, the concentrated reagent solutions are introduced into a region of the reactor that experiences rapid circulation of the fluid in the reactor; i.e. the reagent introduction region in the reactor is exposed frequently to the contents of the reactor.

It is also important to recognize that efficient mixing is necessary at the reagent introduction region, in order to promote the reaction between the concentrated reagents. Because this (efficient) mixing process is carried out by rapid circulation of the reactor fluid through the reagent introduction region, the contents of the reactor are necessarily exposed to the concentrated reagents. From a kinetic view point, the extent of exposure of the reactor contents to the unreacted reagents would depend on the rate of dilution of the concentrated reagents relative the rate of the chemical reaction between the concentrated reagents. Under ideal mixing conditions, the rate of dilution of the concentrated reagents is determined by the molecular/ionic diffusivity of the reactant species; which is still considerably smaller than the rate of the relevant chemical reactions. Hence, the extent of exposure of the reactor contents to the unreacted reagents can be significant even under ideal mixing conditions.

The unintentional exposure of the reactor contents to the unreacted reagents can have undesired effects on the emulsion crystals. For example, exposure of unreacted silver nitrate can result in the creation of fog centers in the crystals.

Furthermore, consistent nucleation conditions are critical to repeatable precipitations. Double jet nucleation using solutions of silver nitrate and soluble halides, depend critically on matched reagent arrival times in this reactor. Small variations in the mixing of the reactants upon arrival in the reactor can result in high levels of variability in the final emulsion grain size or size distribution. Hence, nucleation is generally carried out under conditions of relatively high halide concentrations (high pAg) in order to ameliorate pAg shifts associated with any mismatch in the solution properties or arrival times.

The use of concentrated solutions of silver halide complexes prepared from methylamineformamide and excess halide have been reported as a method for alleviating these concerns. However, methylamineformamide is exceedingly hazardous, and the solvent has been documented as a teratogen (promotes deformity in embryos).

SUMMARY OF THE INVENTION

This invention addresses the need for reducing process variability inherent in double jet precipitation of silver chloride crystals. A solution of hydrated dimethylamine hydrochloride ([Me$_2$NH$_2$]Cl) containing the silver chloride precursor complex [Me$_2$NH$_2$]$_x$[Ag$_m$Cl$_n$], is disclosed as a single source material for silver chloride nucleation processes (as opposed to the prior art of nucleation by double jet precipitation). The solution containing [Me$_2$NH$_2$]$_x$[Ag$_m$Cl$_n$] removes the need to manage two separate reagents for the critical nucleation step in silver chloride precipitation.

DETAILED DESCRIPTION OF THE PREFERRED EMBODIMENTS

Hydrated [Me$_2$NH$_2$]Cl solutions containing novel silver chloride complexes are used as single source materials for nucleation of silver chloride crystals. Solutions containing the silver chloride precursor complex [Me$_2$NH$_2$]$_x$[Ag$_m$Cl$_n$] (where n=m+x and wherein n is 2, x is 1 and m is 1, wherein n is 3, x is 2 and m is 1, wherein n is 4, x is 2 and m is 2, wherein n is 5, x is 3, and m is 2) can be prepared from the following reactions.

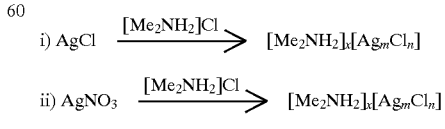

i) AgCl $\xrightarrow{[Me_2NH_2]Cl}$ [Me$_2$NH$_2$]$_x$[Ag$_m$Cl$_n$]

ii) AgNO$_3$ $\xrightarrow{[Me_2NH_2]Cl}$ [Me$_2$NH$_2$]$_x$[Ag$_m$Cl$_n$]

This invention uses the solutions prepared from the above reactions as single source materials for the nucleation of silver chloride crystals. The nucleation process is accomplished by introducing excess water to the hydrated [Me$_2$NH$_2$]Cl solutions containing the precursor complex [Me$_2$NH$_2$]$_x$[Ag$_m$Cl$_n$].

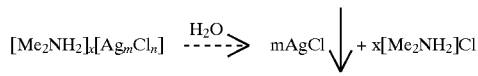

Thus, the amine salt [Me$_2$NH$_2$]Cl can be hydrated and combined with either AgBr or AgNO$_3$ to form solutions containing [Me$_2$NH$_2$][Ag$_m$Cl$_n$].

The following examples illustrate the invention.

EXAMPLE 1

Method A

In a sealed vessel, hydrated [Me$_2$NH$_2$]Cl was heated to approximately 70° C. Then, hydrated silver nitrate was introduced while stirring. The mixture was stirred under the sealed conditions until the silver chloride that initially formed was complexed and a clear colorless solution was observed. The solution was then removed from the heat and allowed to cool to room temperature. Depending on the concentration needed, the final solution contained an amine/silver mol ratio of $\geq 13$. The amine/water mol ratio ranged from 0.6–1.0.

Method B

Hydrated [Me$_2$NH$_2$]Cl was combined with silver chloride in a sealed vessel and the mixture heated to approximately 70° C. The mixture was stirred until a clear colorless solution was observed. Depending on the concentration needed, the final solution contained an amine/silver mol ratio of $\geq 13$. The amine/water mol ratio ranged from 0.6–1.0.

EXAMPLE 2

2.5M AgNO$_3$ and 3M NaCl solutions are added to a 5.5 L aqueous solution containing 0.25 g/L of dithiooctanediol, 4 g/L NaCl, 0.5 g/L poly(ethylene glycol), and 40.91 g/L of regular gelatin. The growth reactor is held at 65° C. resulting in a pAg of approximately 7.17. The solutions are metered in at equal flow rates of 80 cc/min (0.2 moles/min of AgNO$_3$) for 30 seconds. The precipitation is followed by a 30 second no flow stabilization period which is then followed by a ramped flow growth. The mixer was rotated at 2300 rpm.

Control of pAg is initiated at the onset of growth. The AgNO$_3$ flow is ramped to 156 cc/min over a 7.5 minute period. The flow is then held at 156 cc/min until 15 moles of AgCl have been created. NaCl flow will vary to maintain a constant pAg throughout the growth.

Following the growth, the formula was ultrafiltered to three volumetric turnovers to remove excess nitrate salts, some chloride salts, and most of the dithiooctanediol. NaCl was added to the growth reactor prior to washing to bring the pAg down to 7.84 at 40° C. After washing, the emulsion was concentrated to approximately 0.7 kg/Ag mole, the pAg was adjusted to 6.94, and gel was added to bring the final gel concentration to 50 grams of gel per Ag mole.

EXAMPLE 3

A solution of [Me$_2$NH$_3$]$_x$[Ag$_m$Cl$_n$] 1M in silver concentration is precipitated in a 5.5 L aqueous solution containing 0.5 g/L poly(ethylene glycol) and 40.91 g/L of gelatin gel. The growth reactor is held at 65° C. The solution is metered in at 300 cc/min (0.3 mole/min) for 30 seconds. The precipitation is followed by a 30 second no flow stabilization period which is then followed by a same ramped flow growth. The mixer was rotated at 4000 rpm.

2.5M AgNO$_3$ and 3M NaCl were delivered to the growth reactor identical to Example 2, with pAg control. The AgNO$_3$ was ramped from 80 to 156 cc/min in the first 7.5 minutes and then held at 156 cc/min until 15 moles of AgCl have been created.

Following the growth the formula was ultrafiltered to three volumetric turnovers to remove excess nitrate salts, some chloride salts, and most of the remaining dithiooctanediol. NaCl was added to the growth reactor prior to washing to bring the pAg to 7.84 at 40° C. After washing the emulsion was concentrated to approximately 0.7 kg/Ag mole, the pAg was adjusted to 6.94, and gel was added to bring the final gel concentration to 50 grams of gel per Ag mole.

Comparison of the physical grain data is shown below in Table I.

Physical Characterization

TABLE I

| Emulsion | Cubic Edge Length (microns) | Grainsize Distribution | Roundness Index |
|---|---|---|---|
| Example 2 | 0.763 | 1.0693 | 0.261 |
| Example 3 | 0.677 | 1.1032 | 0.281 |

Photographic Performance Evaluation Sensitization

An emulsion sample is melted at 40.0° C., the pH is adjusted to 5.7 and the pAg is adjusted to 7.6 and then, a) Colloidal gold sulfide is added to the emulsion, 4 mg Au$_2$S/Ag mole.

b) The emulsion is heated to 60.0° C. at a rate of 1.67° C./minute.

c) After 18 minutes at 60.0° C., add blue sensitizing dye at 188 mg/Ag mole.

d) After 35 minutes at 60.0° C., add acetamidophenol mercaptotetrazole at 69 mg/Ag mole.

e) After 45 minutes at 60.0° C., add dopant at 0.042 mg/Ag mole.

f) After 49.5 minutes at 60.0° C., add KBr at 0.81 mg/Ag mole.

g) After 64.5 minutes at 60.0° C., the emulsion sample is cooled to 40.0° C. at a rate of 1.67° C./minute.

h) Sample pH is adjusted to 4.9, add KCl at 9.72 g/Ag mole.

i) Emulsion sample is chill-set for later remelting and coating.

Each coating was exposed by a tungsten lamp for 0.1 second followed by processing in Kodak Ektacolor RA-4 chemistry in a roller transport processor. Filtration was a Wratten 48+2B+neutral density. Emulsion coating performance was judged by measuring photographic sensitivity (speed) in relative Log exposure units at a density of 0.8. Shoulder is defined as the density obtained at 0.4 Log exposure more than the speed point. Toe is defined as the density at 0.2 Log exposure less than the speed point. Dmin is the density observed in processed coating without light exposure.

TABLE II

|  | Speed | Shoulder | Toe | Dmin |
|---|---|---|---|---|
| Example 2 | 158.2 | 1.676 | 0.438 | 0.052 |
| Example 3 | 150.2 | 1.252 | 0.548 | 0.113 |

The two emulsions show comparable photographic performance, when the difference in size is taken into account.

The method of precipitating silver chloride is by introduction of the solution containing $[(CH_3)_2NH_2]_x[Ag_mCl_n]$ into an aqueous medium or introducing an aqueous solution to the solution of $[(CH_3)_2NH_2]_x[Ag_mCl_n]$, While the invention has been described with particular reference to a preferred embodiment, it will be understood by those skilled in the art that various changes can be made and equivalents may be substituted for elements of the preferred embodiment without departing from the scope of the invention. In addition, many modifications may be made to adapt a particular situation in material to a teaching of the invention without departing from the essential teachings of the present invention.

We claim:

1. A method of preparing a solution of a dimethylamine silver chloride complex comprising reacting $[(CH_3)_2NH_2]Cl$ with AgCl and water.

2. A method of preparing a solution of a dimethylamine silver chloride complex comprising reacting $[(CH_2)_2NH_2]Cl$ with silver nitrate and water.

3. A solution of a silver chloride precursor complex comprising $[(CH_3)_2NH_2]_x[Ag_mCl_n]$ in water wherein, if n=2, x=1, m=1; if n=3, x=2, m=1; if n=4, x=2, m=2; and if n=5, x=3, m=2.

4. The method of precipitating silver chloride by introducing $[(CH_3)_2NH_2]_x[Ag_mCl_n]$ into water or introducing water to $[(CH_3)_2NH_2]_x[Ag_mCl_n]$ wherein, if n=2, x=1, m=1; if n=3, x=2, m=1; if n=4, x=2, m=2; and if n=5, x=3, m=2.

5. A method of nucleating silver chloride crystals comprising precipitating said crystals from $[(CH3)_2NH_2]_x[Ag_mCl_n]$ in water, wherein if n=2, x=1 and m=1; if n=3, x=2 and m=1; if n=4, x=2 and m=2; and if n=5, x=3 and m=2.

* * * * *